(12) United States Patent
Jelezko et al.

(10) Patent No.: US 10,345,400 B2
(45) Date of Patent: Jul. 9, 2019

(54) METHOD FOR THE HYPERPOLARISATION OF NUCLEAR SPIN IN A DIAMOND VIA A LONG-RANGE INTERACTION

(71) Applicant: UNIVERSITAET ULM, Ulm (DE)

(72) Inventors: Fedor Jelezko, Ulm (DE); Jianming Cai, Neu-Ulm (DE); Martin Plenio, Ulm (DE); Alex Retzker, Ulm (DE); Boris Naydenov, Ulm (DE); Ilai Schwarz, Tel Aviv (IL)

(73) Assignee: UNIVERSITAET ULM, Ulm (DE)

( * ) Notice: Subject to any disclaimer, the term of this patent is extended or adjusted under 35 U.S.C. 154(b) by 419 days.

(21) Appl. No.: 14/783,262

(22) PCT Filed: Apr. 7, 2014

(86) PCT No.: PCT/EP2014/056958
§ 371 (c)(1),
(2) Date: Oct. 8, 2015

(87) PCT Pub. No.: WO2014/166883
PCT Pub. Date: Oct. 16, 2014

(65) Prior Publication Data
US 2016/0061914 A1 Mar. 3, 2016

(30) Foreign Application Priority Data
Apr. 8, 2013 (EP) .................................... 13162810

(51) Int. Cl.
*G01R 33/28* (2006.01)
*G06N 10/00* (2019.01)
*B82Y 10/00* (2011.01)
*G01N 24/12* (2006.01)
*G01R 33/56* (2006.01)
*G01R 33/62* (2006.01)
*G01N 24/00* (2006.01)

(52) U.S. Cl.
CPC ............ *G01R 33/282* (2013.01); *B82Y 10/00* (2013.01); *G01N 24/006* (2013.01); *G01N 24/12* (2013.01); *G01R 33/5601* (2013.01); *G01R 33/62* (2013.01); *G06N 10/00* (2019.01)

(58) Field of Classification Search
None
See application file for complete search history.

(56) References Cited

U.S. PATENT DOCUMENTS

2016/0054402 A1* 2/2016 Meriles ................ G01R 33/282
324/309

OTHER PUBLICATIONS

PCT, "International Search Report for International Application No. PCT/EP2014/056958," dated Jul. 11, 2014.
(Continued)

*Primary Examiner* — Jermele M Hollington
*Assistant Examiner* — Suresh K Rajaputra
(74) *Attorney, Agent, or Firm* — Finnegan, Henderson, Farabow, Garrett & Dunner, LLP (57) ABSTRACT

The invention concerns a method for the hyperpolarisation of $^{13}$C nuclear spin in a diamond, comprising an optical pumping step, in which colour centre electron spins in the diamond are optically pumped. The method further comprises a transfer step in which the polarisation of a long-lived state of the colour centre electron spins is transferred to $^{13}$C nuclear spins in the diamond via a long-range interaction.

20 Claims, 8 Drawing Sheets

(56) References Cited

OTHER PUBLICATIONS

Fischer, R. et al., "Optical polarization of nuclear ensembles in diamond," Physical Review B, 2013, p. 125207-1-125207-7, vol. 87, No. 12, The American Physical Society, USA.

Filidou, V. et al., "Ultrafast entangling gates between nuclear spins using photoexcited triplet states," Nature Physics, 2012, p. 596-600, vol. 8, No. 8, Macmillan Publishers Limited.

King, J. P. et al., "Optical Polarization of <13>C nuclei in diamond through nitrogen vacancy centers," Physical Review B, 2010, p. 073201-1-073201-4, vol. 81, No. 7, The American Physical Society, USA.

Aharonovich, I. et al., "Diamond photonics," Nature Physics, 2011, p. 397-405, vol. 5, No. 7, Macmillan Publishers Limited.

Cai, J. et al., "Diamond-based single-molecule magnetic resonance spectroscopy," New Journal of Physics, 2013, p. 1-21, vol. 15, IOP Publishing Ltd and Deutsche Physikalische Gesellschaft.

Reynhardt, E. C. et al., "Dynamic nuclear polarization of diamond. II. Nuclear orientation via electron spin-locking," Journal of Chemical Physics, 1998, p. 4100-4107, vol. 109, No. 10, American Institute of Physics.

Scheuer, J. et al., "TT 66.8: Lecture: Detecting and Polarizing Nuclear Spins in Diamond," Deutsche Physikalische Gesellschaft (German Physical Society), Mar. 15, 2013, Regensburg, Germany.

Scheuer, J., "Detecting and Polarizing Nuclear Spins in Diamond," Ulm University (uulm), Mar. 15, 2013, Quantum Optics.

C. Belthangady et al. "Dressed-State Polarization Transfer between Bright & Dark Spins in Diamond," arXiv:1211.2749v1 [quant-ph], Nov. 12, 2012.

V. Jacques et al. "Dynamic Polarization of Single Nuclear Spins by Optical Pumping of Nitrogen-Vacancy Color Centers in Diamond at Room Temperature," Phys. Rev. Lett., vol. 102, Issue 5, pp. 057403-1 to 057403-4, Published Feb. 6, 2009.

H-J. Wang et al. "Sensitive magnetic control of ensemble nuclear spin hyperpolarization in diamond," Nature Communications 4, Published Jun. 5, 2013.

\* cited by examiner

METHOD FOR THE HYPERPOLARISATION OF NUCLEAR SPIN IN A DIAMOND VIA A LONG-RANGE INTERACTION

RELATED APPLICATION

The present application is National Phase of International Application No. PCT/EP2014/056958 filed Apr. 7, 2014, and claims priority from European Patent Application No. 13162810.9, filed Apr. 8, 2013, the disclosure of which is hereby incorporated by reference herein in its entirety.

FIELD OF THE INVENTION

The invention concerns a method for the hyperpolarisation of $^{13}$C nuclear spin in a diamond. The invention further comprises a method for the nuclear spin hyperpolarisation of $^{13}$C in a molecule and a method for producing an imaging agent. Additionally, a diamond and uses for such a diamond form part of the invention.

PRIOR ART

In a diamond, electron spins in a particular kind of colour centre, a nitrogen vacancy centre, can be polarised optically.

In "Dressed-State Polarization Transfer between Bright & Dark Spins in Diamond", arXiv:1211.2749v1 [quant-ph], 12 Nov. 2012, C. Belthangady et al. report the polarisation of electron spins in a nitrogen vacancy centre in diamond by optical pumping. The polarisation of the nitrogen centre electron spins can then be transferred to substitutional nitrogen electron spins by applying electromagnetic fields analogous to the Hartmann-Hahn matching condition. In this publication, polarisations are exclusively transferred between electrons and not from electrons to nuclei or between nuclei.

Methods for the hyperpolarisation of $^{13}$C nuclear spin in a diamond are known in the art. In "Optical polarization of nuclear ensembles in diamond", arXiv:1202.1072v3 [quant-ph], R. Fischer et al. report the polarisation of a dense nuclear spin ensemble in diamond. Their method is based on the transfer of electron spin polarisation of negatively charged nitrogen vacancy colour centres to the nuclear spins via the excited-state level anti-crossing of the centre. Fischer et al. have adapted the method to polarise single nuclear spins in diamond based on optical pumping of a single nitrogen vacancy centre defect, which had already been described by V. Jacques et al. in "Dynamic Polarization of Single Nuclear Spins by Optical Pumping of Nitrogen-Vacancy Color Centers in Diamond at Room Temperature", Phys. Rev. Lett., volume 102, issue 5, pages 057403-1 to 057403-4. Both Fischer et al. and Jacques et al. use short-lived states of the colour centre spins, which are not suitable for directly polarising via long-range interactions nuclear spins far away from the colour centre.

In "Sensitive magnetic control of ensemble nuclear spin hyperpolarization in diamond", Nature communication 4 (2013) Hai-Jing Wang et al. show polarisation of nuclear spins in contact interaction with a nitrogen vacancy colour centre in a diamond using the ground state level anti-crossing of the centre. While the colour centre state is long-lived, the experiment demonstrates polarisation of nuclear spins only via then short range contact interaction, which does not diffuse to nuclei further away. Moreover, for the specific polarisation method described in the text, the $T_2$ time of the colour centres in the diamond used correspond to a very short coherence time and is too short for polarising nuclear spins via long ranged interactions.

Eduard C. Reynhardt et al. describe the polarisation of $^{13}$C nuclei by means of nuclear orientation via electron spin-locking (Hartmann-Hahn cross-polarisation between paramagnetic electrons and $^{13}$C nuclei) in a suite of natural diamonds in "Dynamic nuclear polarization of diamond. II. Nuclear orientation via electron spin-locking", J. Chem. Phys. volume 109, number 10, pages 4100 to 4106. Reynhardt et al., however, do not exploit the electron spin of nitrogen vacancy centres and are thus not able to use optical polarisation of the electron spin.

In magnetic resonance applications, it is desirable to reach a higher degree of polarisation of $^{13}$C nuclei throughout a diamond than has hitherto been accomplished.

Problem According of the Invention

The problem to be solved by the invention is to provide a better method for the hyperpolarisation of nuclear spin in a diamond, to supply a diamond with hyperpolarised $^{13}$C nuclei and create a use for such a diamond. In addition to this, an improved method for the nuclear spin hyperpolarisation of $^{13}$C in a molecule and an improved method for the production of an imaging agent is sought.

Solution According to the Invention

The invention solves the problem according to the invention by a method for the hyperpolarisation of $^{13}$C nuclear spin in a diamond, which comprises an optical pumping step and a transfer step. In the optical pumping step, colour centre electron spins in the diamond are optically pumped. In the transfer step, the polarisation of a long-lived state of the colour centre electron spins is transferred to $^{13}$C nuclear spins in the diamond via a long-range interaction.

In the context of the present invention, a long-range interaction is defined as an interaction which decays according to a power law with the distance of the $^{13}$C nuclear spins from the colour centre. Examples are a coherent dipolar interaction, which decays as the distance cubed, and the case of the incoherent dipolar interaction, which decays as the distance to the power of six.

A long-lived colour centre spin state is defined as a state in which the coupling strength of the colour centre spin and nuclear spins is larger than the decay rate of the colour centre spin state for nuclear spins at least 0.5 nm distanced from the colour centre spin.

Furthermore, the problem is solved by a method for the nuclear spin hyperpolarisation of $^{13}$C nuclear spins in a molecule, wherein the molecule is brought near or into contact with a diamond and prior to, during or after that, the diamond is hyperpolarised in the method according to claim 1. In this context, "near" means that the diamond and the molecule are close enough to each other to allow propagation of a nuclear spin's polarisation from a $^{13}$C nucleus of the diamond to a nucleus of the molecule.

Another solution to the problem consists in a method for the production of an imaging agent, wherein a diamond is coupled to a molecule and prior to or after the coupling, the diamond is hyperpolarised in the method according to claim 1. The problem is further solved by the use of a hyperpolarised diamond according to claim 1 in medical or cell based imaging, in a quantum information processor or a quantum sensor based on spin degrees of freedom. Moreover, a diamond with a volume of above 1 nm$^3$, in some embodiments of above 1 μm$^3$, in which diamond the $^{13}$C nuclear spins in the entire diamond are hyperpolarised to at least 0.001% polarization solves the problem according to the invention.

In the context of the present invention, polarization is defined according to the standard definition: the number of $^{13}C$ nuclear spins in the preferred direction minus the number in the opposite direction, divided by the total number of $^{13}C$ nuclear spins.

Point defects in a diamond lattice, in which a vacancy is filled by one or more electrons, are termed colour centres. The electron spins at a suitable colour centre can be polarised by optical pumping. Optically polarised colour centre electron spins can be transferred to surrounding $^{13}C$ nuclear spins to create nuclear polarisation.

A diamond according to the invention can be a synthetic diamond or a naturally occurring diamond. The diamond according to the invention possesses at least one colour centre. Synthetic diamonds according to the invention can be produced, e.g., by chemical vapour deposition (CVD), using detonation or milling of large scale, high pressure, high temperature crystals. High $^{13}C$ nuclear spin polarisation densities can be achieved in diamond as the nuclear density of diamond is higher than in most other available materials. In CVD, advantageously, diamonds enriched for $^{13}C$ can be produced such that an even higher $^{13}C$ nuclear spin polarisation density is achievable.

An imaging agent can be produced by coupling the diamond to a molecule and prior to, during or after the coupling, the diamond is hyperpolarised according to the method described in claim 1. Preferably, the molecule is a biological molecule, such as a protein, and/or a molecule with a high affinity to a biological molecule, such as a drug. Preferably, such imaging agents can bind to specific structures in individual cells or to defined sites in the body of an animal or human. The specific structures of defined sites can then by located by locating the hyperpolarised diamond using MRI. Advantageously, the imaging agent can aid the detection and tracking of specific structures in vivo.

The hyperpolarised diamond according to the invention can be used in medical or cell based imaging. Even though diamond is a chemically inert material, biological molecules can be linked to the surface of diamonds. In particular, it has been demonstrated in "Dynamics of Diamond Nanoparticles in Solution and Cells", Felix Neugart et al., Nano Letters, 2007, volume 7, issue 12, pages 3588 to 3591 (the corresponding portion of which is incorporated into the present disclosure by way of reference) that diamond nanoparticles can be conjugated with biotin, to which streptavidin is able to bind. As many streptavidin-linked biological molecules, in particular proteins, are already commercially available, biotinylated diamond nanoparticles can easily be conjugated to bind specifically to a variety of proteins and cells. As cryogenic temperatures can be avoided, the loss in polarisation during the transfer of the hyperpolarised diamond from the site of polarisation to the MRI scanner can be reduced. Due to the high density of $^{13}C$ nuclei, a much higher signal density can be achieved in diamond than in other hyperpolarised materials.

A hyperpolarised diamond according to the invention can be used in a quantum information processor or a quantum sensor based on spin degrees of freedom. Polarisation of nuclear spin environments reduces the noise that the nuclear environment exerts on the electronic spin degree of freedom. Thus, the invention can allow for improving the coherence times of quantum information processors and quantum sensors based on spin degrees of freedom.

The volume of the diamond is preferably greater than 1 $nm^3$, more preferably greater than 10 $nm^3$, even though diamonds with a volume greater than 1000 $nm^3$ or even greater than 1 $\mu m^3$ or even greater than 10 $\mu m$ or even greater than 1000 $\mu m^3$ are also possible. A preferred diamond has a volume of less than 1000 $nm^3$ more preferably less than 100 $nm^3$. In principle a diamond with an arbitrary size can be polarised with the method according to the invention as long as the concentration of the colour centres is high enough. An attainable advantage of the method according to the invention is that it can be applied at any magnetic field. The methods described in the prior art work only for a particular magnetic field, namely at the level anti-crossing of the NV centre's spin levels.

The use of the dipolar long-range interactions between the colour centre and $^{13}C$ nuclear spins can greatly increase the speed of the polarisation process, as a much larger number of nuclear spins can be polarised directly by the colour centre spin, and the final bulk polarisation achieved. Accordingly, with the invention it is achievable to hyperpolarise nuclear spins in a diamond faster and/or to attain higher overall polarisation.

The invention makes it possible to produce diamond nanoparticles that are hyperpolarised through their entire volume. Such hyperpolarised diamond nanoparticles can lead to large signal to noise ratios in NMR and MRI and can thus increase resolutions, lower the detection threshold and permit faster and dynamic scans. Cells and processes in the body can be imaged with the aid of hyperpolarised diamonds attached to proteins. Advantageously, the method according to the invention can be performed at room temperature; cryogenic temperatures are no longer needed. Furthermore, the method only requires a relatively low magnetic field, which enables the hyperpolarised diamonds to be produced inexpensively, on a large scale and in a relatively simple setup. Such simple setups can be incorporated into a hospital environment more easily, which may lead to a reduction in implementation costs. Additionally, the very long relaxation time of $^{13}C$ nuclear spins in diamond nanoparticles can allow for a long period of time to pass between the polarisation process and the imaging. The duration of this period of time in some embodiments of the invention is greater than 1 minute, in some embodiments even greater than 10 minutes, in some embodiments even greater than 30 minutes. Thus, the polarisation process can be performed in a different location from the imaging, potentially even in a central location for a few hospitals, and can be used for imaging processes in the body with a longer timescale.

Preferred Embodiments According to the Invention

Examples of long-lived colour centre spin states that are suitable for practicing the present invention include the ground state of an NV centre spin in a diamond. The preferred diamond is of high purity, i.e. at most 200 ppm nitrogen nuclei (also referred to as "P1 centres"), more preferably less than 5 ppm nitrogen nuclei. In some embodiments, the invention is practiced a low temperature, e.g. liquid nitrogen temperature (77 K).

In some embodiments, the polarisation of a long-lived excited triplet state, for example in an oxygen-vacancy (2.818 eV), is transferred to the $^{13}C$ nuclear spins.

In preferred methods according to the invention, the long-lived colour centre spin state is a state in which the coupling strength of the colour centre spin and nuclear spins is larger than the decay rate of the colour centre spin state for nuclear spins at least 3 nm, more preferably 5 nm distanced from the colour centre spin. With such very long-lived colour centre spin states, a high hyperpolarisation can be achieved particularly fast.

In preferred methods according to the invention, an external microwave field or radio frequency (RF) field is applied. The external microwave field or radio frequency (RF) field may be continuous or pulsed. The application of the microwave field preferably serves to tune the coupling between the colour centre electron spins and the surrounding $^{13}C$ nuclear spins. Another purpose of the microwave field is, preferably, to narrow the line width of the electron and thus make the transfer of the polarisation of the electron spins to the nuclear spins more efficient. Applying the microwave field in this manner, it is preferably achievable to completely polarise the $^{13}C$ nuclei close to the colour centre. It is an achievable advantage of these embodiments of the invention that the spin polarisation transfer from the colour centres to the $^{13}C$ nuclear spins can be accelerated. Many DNP protocols as discussed below involve the application of an external microwave field or a radio frequency (RF) field.

According to some embodiments of the invention, the long range interaction is achieved by using dipolar interaction between the colour centre electron spin and the $^{13}C$ nuclear spins. According to some embodiments, the polarisation is transferred by a standard dynamic nuclear polarisation (DNP) protocol for using dipolar interactions to transfer electron polarisation to surrounding nuclear spins. In the context of the present invention, DNP protocols are defined as protocols for transferring the polarization from an electron spin is to the $^{13}C$ nuclei by microwave or RF irradiation of the sample. Advantageously, by means of a DNP the transfer of the polarisation from the electron spins to the surrounding nuclear spins can be accelerated.

Examples for suitable DNP protocols include the solid effect, the cross effect, thermal mixing, and pulsed DNP methods such as the NOVEL sequence or dressed-state solid effect. A review of many current DNP protocols can be found in Maly, Thorsten, et al. "Dynamic nuclear polarization at high magnetic fields." J Chem Phys. 2008; 128(5): 052211 (see section II. "Polarizing mechanisms in DNP experiments"). Most DNP protocols involve either interactions between electron spins or are based on two underlying physical mechanisms: fulfilling the Hartmann-Hahn condition and excitation of selective transitions (i.e. irradiation at a frequency matching the energy gap between two quantum states). The DNP protocols differ in the configurations for achieving these conditions and by the usage of microwave pulses or continuous microwave radiation.

According to the invention, the DNP protocols can be used for fulfilling the Hartmann-Hahn condition between the colour centre spin and the $^{13}C$ nuclear spins or for excitation of selective transitions caused by the dipolar interaction of $^{13}C$ nuclear spin states with the colour centre spin. The general concept of Hartmann-Hahn double resonance as described in Hartmann, S. R. and Hahn, E. L., "Nuclear Double Resonance in the Rotating Frame", Physical Review, 1962, vol. 128, Issue 5, pp. 2042-2053, relevant portions of which are incorporated into the present disclosure by way of reference.

According to some DNP protocols, the Hartmann-Hahn condition is achieved. This condition requires that the Rabi frequency of the electron spin be equal to the Larmor frequency of the $^{13}C$ nuclear spins in some reference frame (both the Rabi frequency and Larmor frequency can be between dressed or bare eigenstates). In this case mutual spin flip-flops are allowed and the high electron spin polarisation can be transferred to the nuclear spins. Thus, transferring of the polarisation of the colour centre electron spins to the $^{13}C$ nuclear spins can be achieved. Preferably, the DNP method termed NOVEL is used to transfer spins from the colour centre electrons to the $^{13}C$ nuclei. In NOVEL, preferably, a pi/2 rotation is carried out, followed by spin locking for an adequate time for the transfer of the colour centre electron spin to the $^{13}C$ nuclear spin to occur. After the Hartmann-Hahn condition has been achieved, it is also possible to not use spin locking and simply wait for a spin flip-flop between the electron and the nuclear spin to occur, which can also lead to the polarisation transfer from the colour centre electrons to the surrounding $^{13}C$ nuclei. Preferably, the Hartmann-Hahn condition is achieved by a microwave field or a radio frequency field, the intensity of the field being chosen to match the energy difference between dressed colour centre electron spin eigenstates and the $^{13}C$ nuclear spins in an external magnetic field.

Alternatively, the Hartmann-Hahn condition between NV-centre electron spin and external nuclear spins can also be achieved by means of optical Raman fields at low temperatures, preferably below 10 K, which couple the electronic spin states via an optically excited state obtained by tuning a magnetic field to an excited state anti-crossing to enable individual addressing. For other solid state based systems such as chromium in ruby the use of optical Raman fields is possible at room temperature.

The magnetic flux density of the external magnetic field is smaller than 3 T. The method according to the invention allows for the use of external magnetic fields with a low magnetic flux density, preferably below 2 T, more preferably below 1 T and most preferably below 0.5 T. Advantageously, these magnetic flux densities can be achieved by a permanent magnet or an electromagnet, which does not rely on liquid cooling.

Another preferred method for using the long-ranged interaction, according to some embodiments, involves excitation of selective transitions caused by the dipolar interaction of $^{13}C$ nuclear spin states with the colour centre spin. Focusing on a two particle system of the colour centre spin and a $^{13}C$ nuclear spin, the dipolar interaction causes a shift in the energy level of the combined two-spin quantum system. This shift induces different energy gaps between the two spin system states, meaning that each transition between states has a unique energy gap. This allows for external excitation of only one selected transition using pulses or continuous waves in a specific frequency tuned to the energy gap of that particular transition. Excitation of the transition between the state where the colour centre spin is polarised and the $^{13}C$ nuclear spin is not polarised to the opposite state (polarised $^{13}C$ nuclear spin, non-polarised colour centre spin) induces a polarisation transfer, used in the solid effect DNP protocol.

In some methods according to the invention the transfer step is performed by interaction involving at least two colour centre spins and a nuclear spin. This mechanism (used in the cross effect and thermal mixing DNP protocols) is based on allowed transitions of several electron spins and a nuclear spin involving a homogeneously or inhomogeneously broadened EPR line. The broadening of the EPR lines allow a simultaneous flip of two or more electron spins and a nuclear spin to be energy conserving and enables transfer of the electron spins' polarization to the nuclear spins with the correct microwave irradiation.

The colour centres in diamond used in the method according to the invention can achieve a much higher electron spin polarisation compared with the nitrogen spins used in previous studies.

Preferably, in the methods according to the invention the diamond's $^{13}$C nuclear spin polarisation is far above thermal equilibrium conditions. Preferably, the diamond's $^{13}$C nuclear spin polarisation is by a factor of at least $10^3$, more preferably at least $10^4$ and most preferably at least a factor of $10^5$ above thermal equilibrium conditions. Due to such hyperpolarisation, such diamonds can easily be detected in nuclear magnetic resonance (NMR) and magnetic resonance imaging (MRI). The above is particular in contrast to prior art methods in which only nuclear spins in $^{13}$C nuclei very close to the colour centre can be polarized, leading to a considerably lower polarization of the diamond as a whole.

In preferred embodiments of the invention the $^{13}$C nuclear spin polarisation in the diamond is greater than 1%. For example, a nano-diamond with 100 $^{13}$C spins with 51 in the preferred direction and 49 in the opposite direction would have a polarization of 2% Preferably the $^{13}$C nuclear spin polarisation is greater than 7%, more preferably greater than 10%, more preferably greater than 15%, more preferably greater than 20%, more preferably greater than 30%, more preferably greater than 50%, and most preferably greater than 70%.

Preferably the colour centre, in which the electron spins are optically pumped, is a nitrogen vacancy (NV) centre. One common colour centre in diamond is known as an NV centre, in which a nitrogen atom substitutes a carbon atom leading to a vacancy in the lattice. An NV centre is especially suited for the optical pumping of its electron spins. Yet, atom substitutes other than nitrogen are also possible for forming a colour centre, e.g. Silicon.

Preferably, the optical pumping step and the transfer step are repeated cyclically. After the optical pumping of the NV centre electrons, the electron spins can be transferred to the surrounding $^{13}$C nuclei. By repeating the optical pumping step and the transfer step, it is achievable to polarise most, preferably all $^{13}$C nuclear spins in close proximity to the NV centre. Preferably, a pause after each cycle allows for the $^{13}$C nuclear spin polarisation to spread from $^{13}$C atoms adjacent to the NV centre throughout the diamond. The propagation of the $^{13}$C nuclear spins may occur spontaneously. Advantageously, no application of alternating electromagnetic fields may be required during the diffusion of nuclear spin from $^{13}$C nuclei close to the NV centre to $^{13}$C nuclei further away. By cyclically repeating the optical pumping step, transfer step and pause, the invention permits the polarisation of preferably more than 10%, more preferably more than 50%, more preferably more than 80%, more preferably more than 90%, more preferably more than 95% and most preferably all of the $^{13}$C nuclei within the diamond.

Preferably, the method is carried out for less than 10 minutes, more preferably, less than 5 minutes, more preferably less than 1 minute, most preferably less than 10 seconds are required to achieve hyperpolarisation in the entire diamond. Preferably, in this method, the diamond has a volume of at least 1 nm$^3$, more preferably at least 10 nm$^3$, even though diamonds with a volume of at least 1000 nm$^3$ or even at least 1 μm$^3$ or even at least 10 μm or even at least 1000 μm$^3$ are also possible. Advantageously, applying the method according to the invention, hyperpolarisation can be achieved rapidly, even in a large diamond. Small diamonds can easily be adapted to medical purposes, in particular as medical imaging agents for MRI. Furthermore, nanoscale diamonds can be taken up into cells by endocytosis, which permits cell based imaging.

Preferably, the optical pumping is performed with a least one laser pulse. A laser is the preferred light source for carrying out the electron spin polarisation of the colour centres. Using a laser, the optical pumping can be achieved efficiently.

Preferably, the method according to the invention is carried out at a temperature above 10 K. More preferably, the method is performed at a temperature greater than 80 K, more preferably greater than 200 K, more preferably greater than 273 K and most preferably at a temperature above 288 K. Preferably, cryogenic temperatures are not needed to polarise a diamond according to the invention. After transfer of the electron spin to the $^{13}$C nuclear spin, the colour centre electron spins can be polarised again by optical pumping. In this way, the colour centre electron spin can preferably serve as a near-zero temperature electron bath, allowing the bulk diamond to be kept at a higher temperature, preferably room temperature.

The preferred diamond according to the invention is a synthetic diamond. Synthetic diamonds can be enriched for $^{13}$C to allow for even larger polarisations to be created. Furthermore, synthetic diamond material can be synthesised inexpensively in a variety of shapes and sizes, including the deposition of diamond on the surface of other materials, e.g., by CVD. At least 1% of the carbon atoms in the diamond are preferably $^{13}$C. More preferably, the diamond is enriched for a $^{13}$C isotope concentration between 5% and 20%, more preferably between 10% and 15%, even though much higher concentrations of $^{13}$C isotopes are possible.

In one preferred embodiment according to the invention, the diamond is coated with a non-diamond material. The coating can take place before or after the hyperpolarisation. A preferred coating yields a higher biocompatibility of the diamond when injected into the bloodstream.

In method for the nuclear spin hyperpolarisation of nuclear spins in a molecule according to the invention, the molecule is brought near or into contact with a diamond comprising one or more colour centre(s).

The nuclear spins of the molecule can then be polarised. In a preferred method of polarising the nuclear spins in a molecule the $^{13}$C nuclear polarisation is allowed to propagate from the diamond to the molecule. For this, preferably, the molecule is attached to the diamond; more preferably, the molecule is covalently attached to the diamond. The diamond's $^{13}$C nuclear spin may be hyperpolarised according to the invention with the molecule already near or in contact with the diamond, the molecule may be put near or in contact with the diamond $^{13}$C nuclear spin already hyperpolarised according to the invention, and/or the diamond and the molecule are brought near or in contact during hyperpolarisation of the diamond's $^{13}$C nuclear spin. The spin diffusion is made possible by the dipolar coupling between the $^{13}$C nuclear spins in the diamond and the non-zero nuclear spins in the molecule. Preferably, for the propagation of the nuclear spin polarisation from the diamond's $^{13}$C nuclei to the molecule's nuclei to be efficient, the diamond and the molecule are closer than 1 nm to each other. Possibly, the molecules can then be separated from the diamond. Preferably, after transfer of polarisation to the molecule, the molecule can be scanned in an NMR or MRI scanner. In this way, even small amounts of the molecule can be detected.

Thus, the invention offers a better method for the hyperpolarisation of nuclear spin in a diamond and, furthermore, supplies a diamond with hyperpolarised $^{13}$C nuclei. Moreover, uses for such a diamond and improved methods for nuclear hyperpolarisation in a molecule and for the production of an imaging agent are provided.

DESCRIPTION OF SPECIFIC EMBODIMENTS OF THE INVENTION

Experimental Setup

Figure 1A:
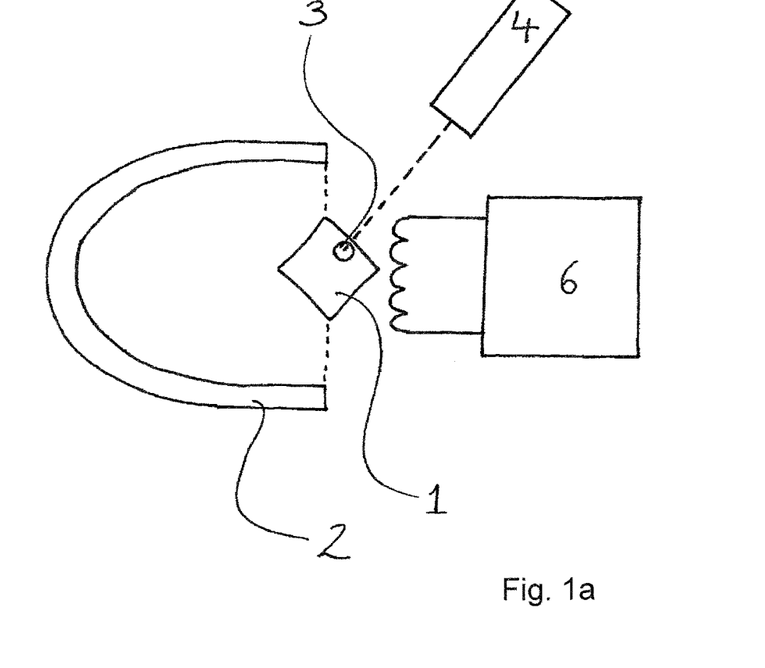
FIG. 1 shows the experimental setup in two conceptual representations.
Figure 1B:
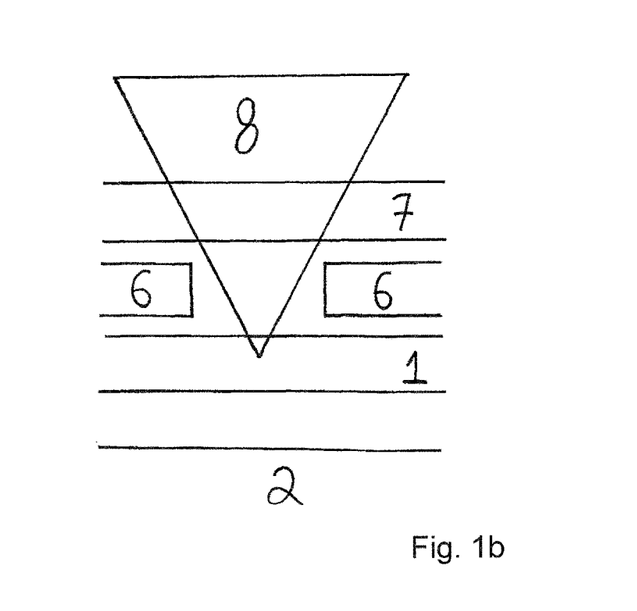

FIG. 1a conceptually details the experimental setup with a diamond 1 placed in the magnetic field of a permanent magnet 2. The diamond 1 contains a colour centre 3, which is an NV centre. A laser 4 serves to excite a colour centre 3 electron. In order to move the diamond 1 into the focus of the laser 4, the diamond 1 is mounted on a piezo stage (not shown). The magnet 2 is mounted on rotation/translation stages 5 (not shown) to be able to align the magnetic field with the crystallographic axis of the colour centre 3. A microwave source 6 allows facilitation of polarisation transfer from electron to $^{13}C$ nucleus. In the conceptual representation of the experimental setup in FIG. 1b, the diamond 1 is placed between the permanent magnet 2 and the microwave source 6, which allows for the Hartmann-Hahn double resonance to be generated in the diamond 1. The optical path 8 of the laser 4 (not shown) is directed through a glass coverslip 7 and focussed into the diamond 1 in order to polarise the electrons in an NV centre.

Diamond Material

The following experiments were performed in a synthetic diamond layer formed by CVD doped with NV centres during growth. The sample used in these experiments possesses two layers with different properties, the substrate and a CVD grown layer. The substrate is a type IIa diamond 1 with a (111) cut and a natural abundance of $^{13}C$. The CVD grown layer is also a (111) cut with a natural abundance of $^{13}C$ and a 1 ppm concentration of phosphorus donors. The donors were added to stabilise the charge state of the NV centre. For some of the dynamic nuclear polarisation protocols a different donor concentration is preferable, and will be mentioned in the description.

For the direct polarisation of external spins via NV centres, ultra-small nanodiamonds, i.e. diamonds with volume between 1 $nm^3$ and 1000 $nm^3$, are preferable. Polarisation transfer will be enabled by dipolar interactions between NV centre spins and external nuclear spins. In addition, it is possible to use other electron spins as mediators for spin polarisation. Alternatively, nitrogen (P1 centre) present in 100 ppm or higher concentration in synthetic high pressure high temperature diamond can be used for this purpose.

Confocal Microscopy of Single NV Centres

Single NV centres were detected using a confocal microscopy technique. A laser beam diode pumped solid state laser 4 operating at 532 nm was focussed onto a diffraction limited spot using a high numerical aperture microscope objective (Olympus UPLAPO 60×). The sample was scanned using a piezo driven stage (nPoint, Inc.). Fluorescence was collected by the same microscope objective and focussed on avalanche photodiodes with single photon sensitivity (SPCM-AQRH, Excelitas). By observation of photon-antibunching, it could be detected that an individual NV centre was in focus. Fluorescence detection of magnetic resonance on single electron spin is based on optical contrast of spin states associated with NV centres.

Microwave Excitation

Figure 2:
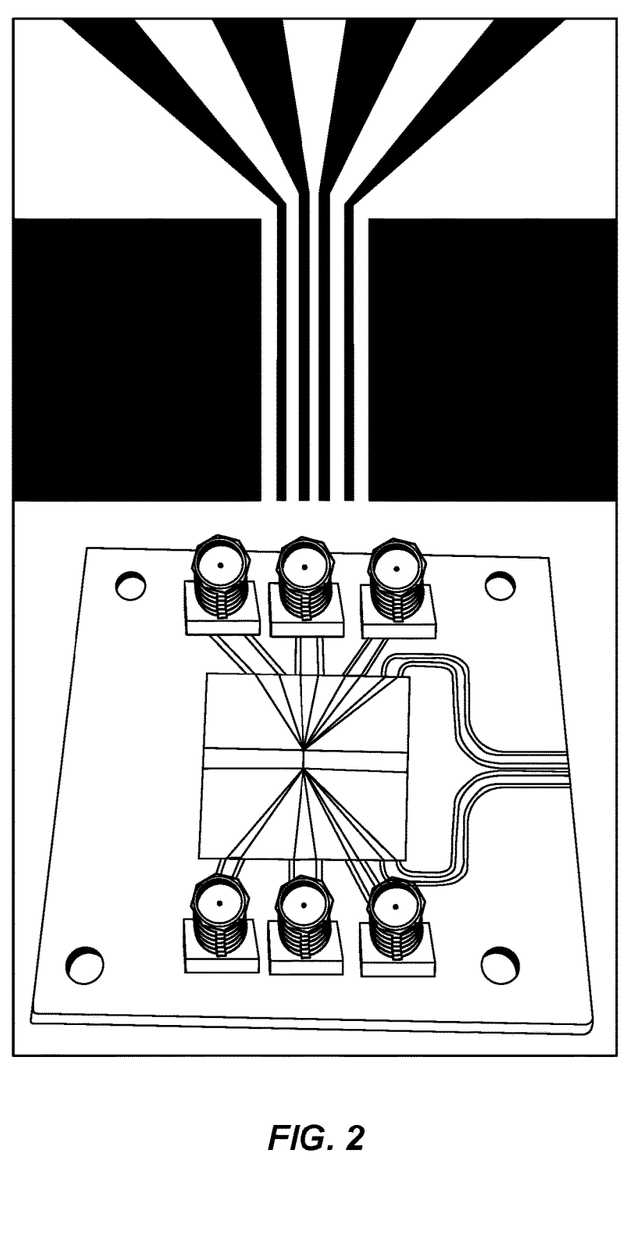
FIG. 2 shows at the top an optical microscope picture of the fabricated structure on glass used in magnetic resonance experiments. At the bottom, a picture of the holder with the strip line structure is displayed.

In order to excite microwave transitions of single colour centres 3 in diamond 1, the sample was placed on a home built microwave strip line providing efficient excitation of the diamond 1. At the top in FIG. 2, an optical microscopic picture of the structure is shown, which was fabricated on a glass cover slip by conventional photolithography and was used in the magnetic resonance experiments. The width and gap of each microstrip is 20 μm. At the bottom in FIG. 2, a picture of the holder with the strip line structure can be seen. The signal is applied via coaxial cables connected to SMA connectors and matched to the two coplanar microstrips.

A commercial microwave source 6 (Anritsu MG 37020A) was used in the experiments. In order to achieve Rabi frequencies of a few MHz, the source was amplified using a commercial high power microwave amplifier (10 W, Gigatronics GT 1000A). Phase control of microwave fields was achieved using commercially available phase shifters (Narda, Inc.). Microwave pulses were formed using commercial microwave switches (General Microwave, F9914). The strength of the microwave drive was controlled by the output level of the microwave source 6.

Figure 3:
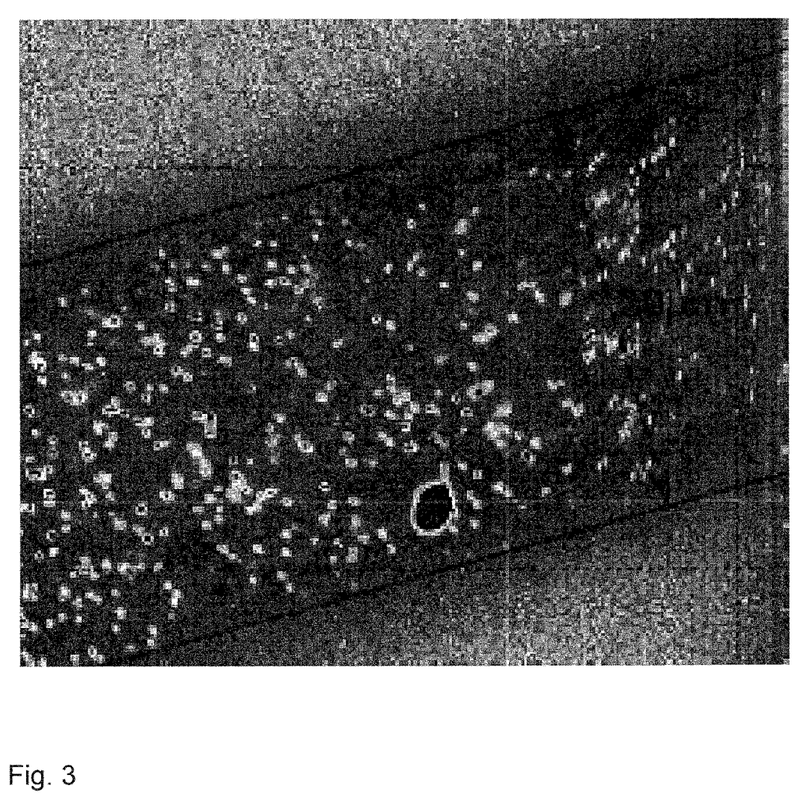
FIG. 3 shows a confocal map of single NV centres adjusted to a microwave stripline.

In FIG. 3, the fluorescence image of a diamond 1 sample on top of the 4-strip microstructure is shown. On the top and the bottom of the image, one strip is displayed each. Between the strips, the diamond area can be seen. Bright spots correspond to the fluorescence emissions of NV centres.

Magnetic Field Control

Figure 4:
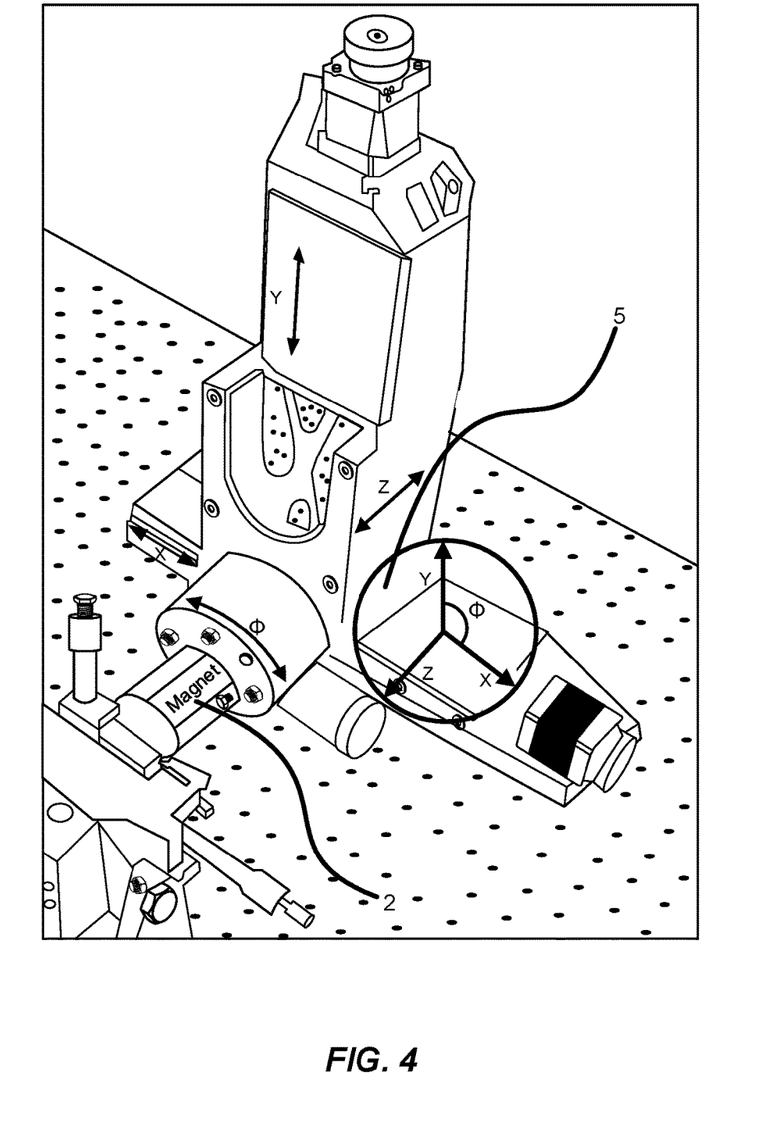
FIG. 4 shows a photo of the magnet stage with a cylindrical magnet attached.

Experiments were performed in a magnetic field on the order of 0.4 T generated by a permanent magnet 2 (magnets4you GmbH) located about 100 μm from the diamond face. In order to align the magnetic field with the crystallographic axis (z-axis) of the NV defect, the magnet 2 was moved using rotation and translation stages 5 (Micos GmbH), as shown in FIG. 4. For ensemble experiments aiming to polarise large samples, magnetic field need to be homogeneous enough to fulfil resonance conditions for the whole sample. Permanent magnet arrangements or electromagnets can be used for this purpose.

Time Resolved Measurements

Optical pulses for optical spin polarisation and time resolved detection of magnetic resonance were produced using acousto-optical modulators (Crystal Technology). Microwave, optical pulses, sample scanning and data acquisition were synchronised by a computer controlled pulse generator (Tektronix, DTG) connected to drivers of acousto-optical modulators, microwave switches and a fast photon counter (FastComtec, P7998).

The optical detection of magnetic resonance was carried out in accordance with the scientific publications Jelezko, F. et al., "Single defect centres in diamond: A review." Physica Status Solidi (a) Applications and Materials Science, 2006. 203(13): pages 3207 to 3225, Jelezko, F. et al., "Read-out of single spins by optical spectroscopy.", Journal of Physics-Condensed Matter, 2004. 16(30): pages R1089 to R1104 and Jelezko, F., et al., "Observation of coherent oscillations in a single electron spin", Physical Review Letters, 2004. 92(7), the relevant portions of which are incorporated into the present disclosure by way of reference.

Polarisation of Electron Spin

Electron spins associated with NV centres were polarised by the application of a short (300 ns) laser 4 pulse. Optical pumping was achieved by excitation of the NV centre into an excited electronic state. The decay of this state occurs predominantly into one of the spin sublevels of the ground state.

Dynamical Polarisation Transfer from Electron Spin to Nuclear Spin

Exchange of polarisation between optically pumped electron spin of NV centre and nuclear spins can be performed using several established dynamic nuclear polarisation protocols, e.g. the solid effect, the cross effect, thermal mixing, the NOVEL sequence and more. Most of these protocols either involve interactions between electron spins or are based on two underlying physical mechanisms: fulfilling the Hartmann-Hahn condition and excitation of selective transitions. The DNP protocols differ in the configurations for achieving these conditions and by the usage of pulses or continuous waves.

For the above DNP protocols, the experimental setup is similar, with the difference in the microwave frequency, pulse sequence and/or magnetic field strength. We used the same equipment for all three protocol examples detailed below, as all three protocols are in the regime of our equipment.

The solid effect (excitation of forbidden transition involving double, electron nuclear spin flips using microwave driving) followed by electron spin relaxation is known to induce efficient polarisation transfer. Notably, the weak electron spin relaxation process can be significantly enhanced by optical pumping of NV centre.

Figure 5:
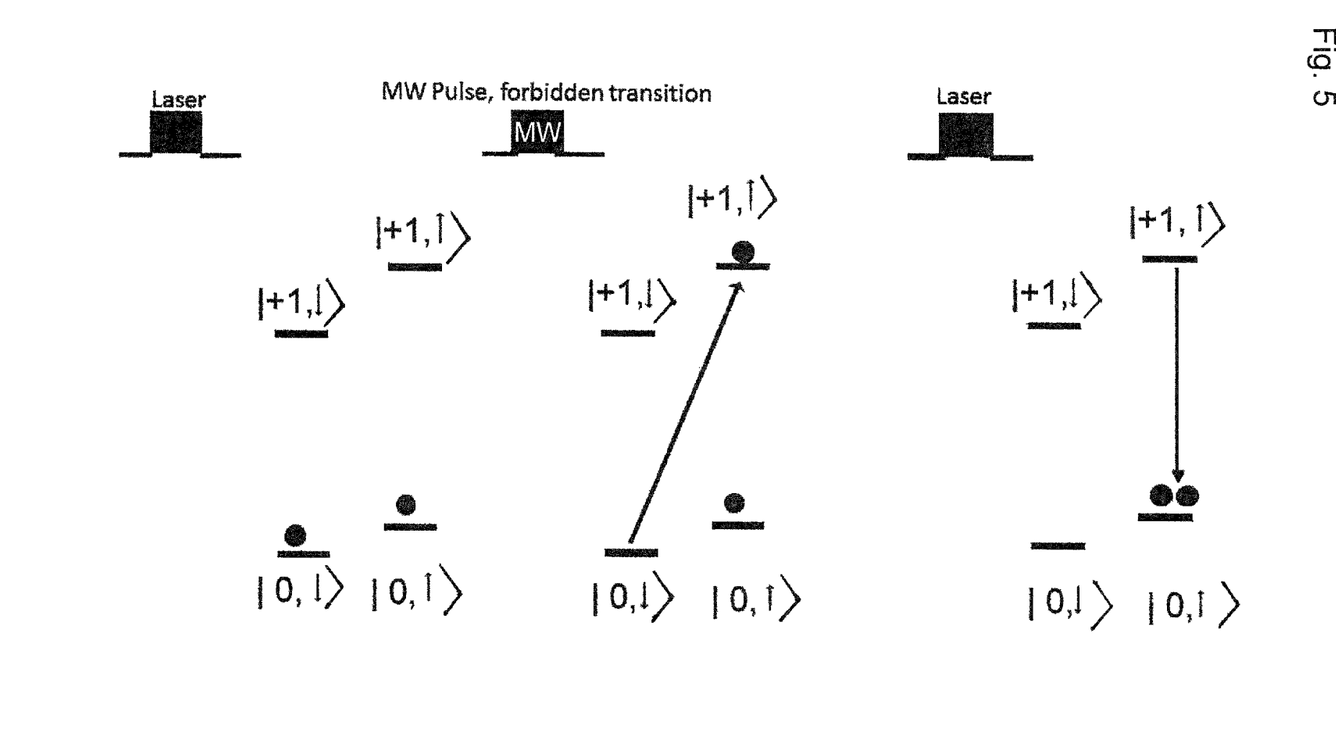
FIG. 5 shows a graphical representation of the polarisation transfer protocol using the solid state effect.

A rigorous theoretical treatment of the solid effect has been performed in numerous papers, e.g. Abragam A, Goldman M. Rep Prog Phys 1978; 41:395, W. T. Wenckebach Applied Magnetic Resonance 2008, 34, 227-235. A graphical representation of the polarisation transfer protocol using the solid state effect is shown in FIG. 5.

At the first stage the laser polarises the NV centre by optical pumping, as described above. Next, via the forbidden transition a microwave excitation excites simultaneously the NV spin and the nuclear spin which results in nuclear polarisation. The NV spin is then re-polarised via optical pumping.

Figure 6:
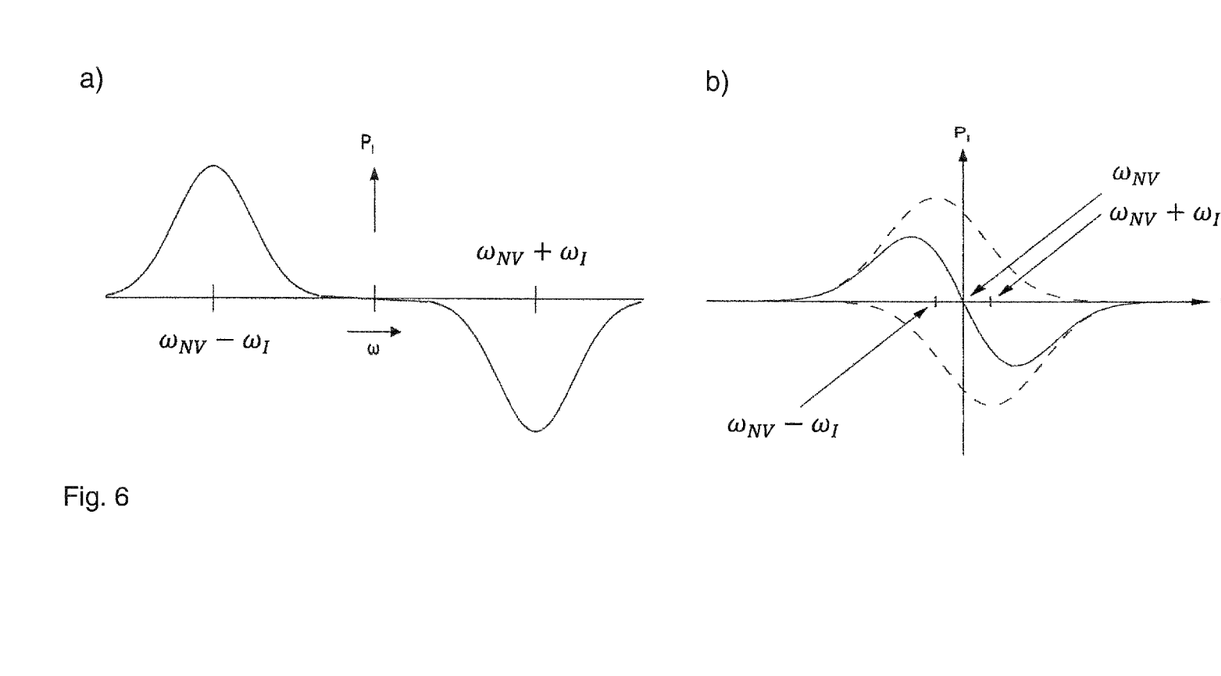
FIG. 6 shows the difference in nuclear polarisation build-up depending in the ESR line width compared to the Larmor frequency.

The rate of polarisation transfer is maximal for microwave frequencies corresponding to the energy levels of the forbidden transitions $\omega_+ \approx \omega_{NV} - \omega_I$ for positive nuclear polarisation and $\omega_- \approx \omega_{NV} + \omega_I$ for negative nuclear polarisation, where $\omega_{0S}$ denotes the NV spin Rabi frequency and $\omega_I$ the nuclear spin Larmor frequency in the lab frame. As the polarisation rate is a function of the NV centre spin ESR line shape, effective polarisation transfer is achieved when the ESR line is narrow compared with the nuclear spins Larmor frequency (or the longitudinal hyperfine component of the interaction with the NV centre spin). The difference in nuclear polarisation build-up depending in the ESR line width compared to the Larmor frequency is depicted in FIG. 6. FIG. 6(a) depicts the nuclear polarisation as a function of the microwave frequency for the case where the nuclear Larmor frequency ($\omega_I$) is larger than the NV centre ESR line. This case is known as the "well resolved solid effect". FIG. 6(b) depicts the nuclear polarisation for the case where the ESR line is not narrow compared to the nuclear Larmor frequency, which is known as the "differential solid effect". In this case, the effects for positive nuclear polarisation and negative nuclear polarisation—depicted in dashed lines in FIG. 6(b)—overlap, reducing the overall polarisation reached (solid line).

Larmor frequencies of $^{13}C$ nuclear spins were approximately 5 MHz for magnetic fields used in our experiments, though stronger magnetic fields can be used for larger Larmor frequencies. For narrow NV centre ESR lines, diamonds with a small concentration of P1 (Nitrogen) donors (less than 10 ppm) are preferable. For instance, CVD grown diamonds with 10 ppm P1 donor will result in NV centre ESR line width which is only limited by $^{13}C$, thus enabling efficient polarisation. Polarisation transfer is then enabled by continuous laser 4 optical pumping combined by resonant microwave 6 irradiation.

An alternative method for transferring the NV centre spin polarisation to the nuclear spins is the so-called cross polarisation effect, involving two electron spins and one nuclear spin. This effect is particularly interesting for samples having high concentration of NV centres with strongly dipolar coupled electron spins. The basis for the cross effect are two dipolar coupled electron spins under the condition that the resonance frequency the electrons is separated by the nuclear Larmor frequency. Thus, the cross-effect can only occur if the inhomogeneously broadened ESR lineshape has a linewidth broader than the nuclear Larmor frequency, contrary to the condition for effective polarisation via the solid effect. An additional condition for the cross effect is that the homogeneously broadened ESR linewidth is narrower than the nuclear Larmor frequency.

The cross effect was first discovered in the 1960s by Kessenikh et al. In Kessenikh et al. Phys Solid State 1963; 5:321, and later by Wollan DS. Phys Rev B 1976; 13:3671. In the last few years, it has again aroused interest after experiments which have shown a large DNP enhancement to the NMR signal in high magnetic fields (e.g. Hall et al. Science 1997; 276:930, . Song et al. J Am Chem Soc 2006; 128:11385).

The cross effect is based on a three spin interaction (two electron spins and a nuclear spin) satisfying the relation:

$$\omega_{s2} - \omega_{s1} = \omega_I, \quad (1)$$

with $\omega_{s1(2)}$ denoting the EPR frequency of electron 1(2) and $\omega_I$ denoting again the Larmor frequency of the nuclear spin.

Figure 7:
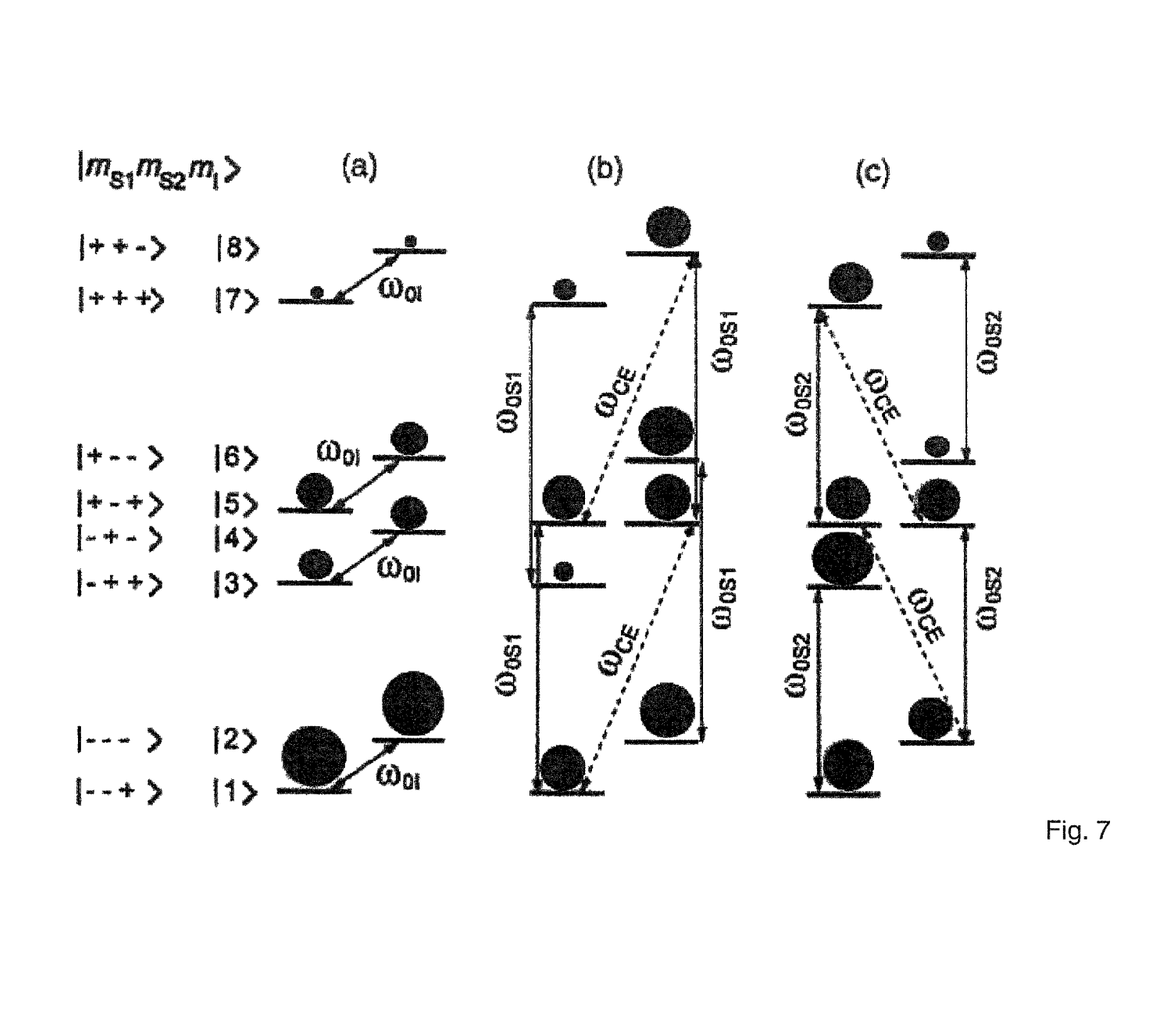
FIG. 7 shows the process of microwave driven polarisation transfer based on the cross effect is shown.

For driving the polarisation transfer, a microwave irradiation is added of frequency $\omega_{s1(2)}$, leading to a negative (positive) nuclear polarisation. The polarisation process is depicted in FIG. 7. FIG. 7(a) depicts the population distribution at thermal equilibrium for a general three spin system (two electron spins and a nuclear spin) in an external magnetic field. In FIG. 7(b and c), the energy level have been set such that condition 1 is met. FIG. 7(b) depicts the new population distribution under microwave irradiation of frequency $\omega_{s1}$, which leads to a saturation of the allowed EPR transitions. As can be seen, this corresponds with negative nuclear polarisation. Microwave irradiation of frequency $\omega_{s2}$ leads to positive nuclear polarisation, see FIG. 7(c).

For a typical diamond with 100 ppm P1 donors, the homogeneus broadening could be ~100 KHz, and the inhomogeneus broadening is typically in the MHz range, but can be made larger by growing the diamond with intrinsic strain along some axis, or by increasing the $^{13}$C concentration in the diamond. Additionally, one could imagine using the P1 donors' electron spin as a pair for the dipolar coupling in the cross effect with the NV centre spins.

Another proposed experimental realization of a DNP protocol for the polarisation transfer is achieved by establishing a Hartmann-Hahn condition between the electron and nuclear spin. This is achieved by driving the electron spin transitions between ms=0 and ms=−1 state by means of a microwave field whose intensity is chosen to match the energy difference between dressed electronic spin eigenstates and the nuclear spins in an external magnetic field.

The dynamics of the NV electronic spin and an additional nuclear spin, in the presence of a continuous driving microwave field have been theoretically analysed in Cai, J.M. et al., "Diamond based single molecule magnetic resonance spectroscopy", New Journal of Physics, 2013, 15, 013020, http://arxiv.org/abs/arXiv: 1112.5502 and the article's supplementary information; the relevant portions of the publication and the supplementary information are incorporated into the present disclosure by way of reference. The Hamiltonian describing the NV centre electronic $m_s$=0, −1 states and an additional $^{13}$C nuclear spin, in the presence of an external magnetic field B and a resonant microwave field is $$H = \Omega\sigma_z \otimes 1 + \gamma_N I \otimes |B_{eff}|\sigma_z + \gamma_N A_{hyp}\sigma_x \varnothing(\sin\theta\sigma_x + \cos\theta\sigma_z) \quad (1)$$

where $\Omega$ is the Rabi frequency of the driving field and $\sigma$ are the spin-1/2 operators, defined in the microwave-dressed basis $$|\pm\rangle = \frac{1}{\sqrt{2}}(|0\rangle \pm |-1\rangle)$$

for the electronic basis, and in the $(|\uparrow z'\rangle, |\downarrow z'\rangle)$ basis for the nuclear spins, where z' is defined along the direction of $B_{eff}$. $B_{eff}$ is an effective magnetic field and is given by $B_{eff}$=B−(1/2)$A_{hyp}$, where $A_{hyp}$ is the hyperfine vector which characterises the coupling between the two spins. In equation (1), $\gamma_N$ is the gyromagnetic ratio of the nuclear spin and cos θ=ĥ·b̂, where ĥ and b̂ are the directions of the hyperfine vector $A_{hyp}$ and the effective magnetic field $B_{eff}$, respectively. The first two terms in the Hamiltonian form the energy ladder of the system ($\Omega$ for the dressed NV spin, and $\gamma_N|B_{eff}|$ for the Larmor frequency of the nuclear spin), whereas the last two terms are responsible for electron-nuclear spin interaction. Here, the former represents mutual spin-flips, or coherent evolution of the electron-nuclear pair, and the latter is the nuclear spin dephasing caused by electron flips. When the driving field is adjusted properly, an energy matching condition (known as the "Hartmann-Hahn condition") given by $$\Omega = \gamma_N|B_{eff}| = \gamma_N|B - (1/2)A_{hyp}|, \quad (2)$$

can be engineered, equalising the first two terms in Hamiltonian (1). Then, the coupling term in the Hamiltonian becomes dominant, and the time evolution of the system is a coherent joint evolution of the electron nuclear pair. For instance, starting in the $|+,\downarrow\rangle$ state, the system evolves according to $|\Psi\rangle=|+,\downarrow\rangle\cos(Jt) + |-,\uparrow\rangle \sin(Jt)$, with J given by $$J = 1/4\gamma_N|A_{hyp}|\sin\theta. \quad (3)$$

Thus, at time t=π/2J the two spins become maximally entangled, and after a t=π/J a full population transfer occurs and the states of the two spins are in effect 'swapped'.

Figure 8:
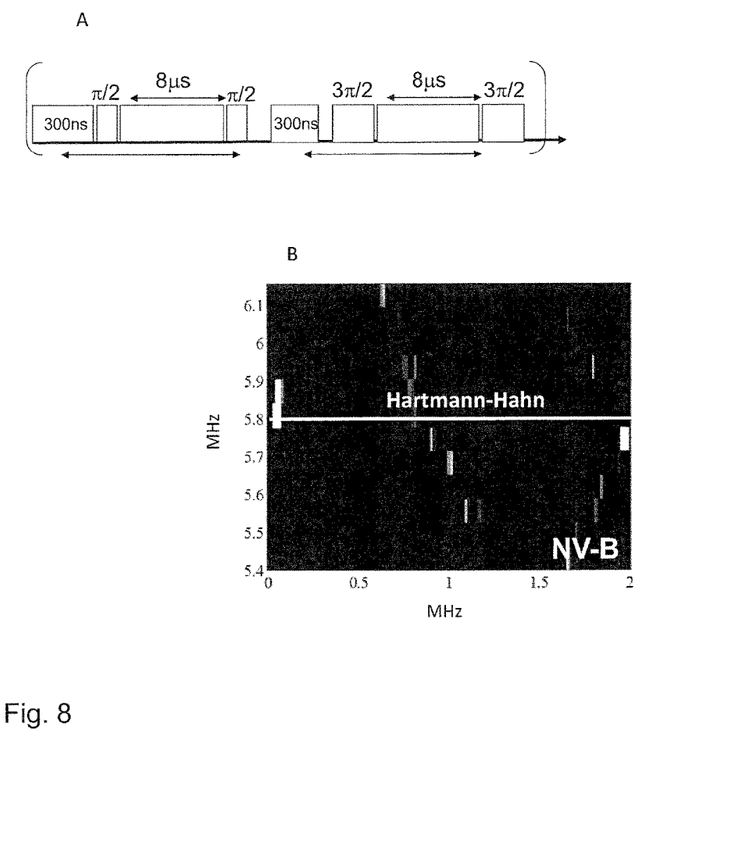
FIG. 8 displays the pulse sequence that was used to polarise nuclear spins on the left and on the right, it shows the low frequency components in the spin-locking signal on the x-axis for various microwave driving fields with the corresponding Rabi frequency on the y-axis.

Larmor frequencies of $^{13}$C nuclear spins were approximately 5 MHz for magnetic fields used in our experiments. In order to transfer the electron spin to the nuclei, we applied a sequence, in which a short laser 4 pulse (300 ns) is used for the polarisation of the electron spin in the ground state of the NV centre and for readout of the population via spin-dependent fluorescence. The microwave manipulation is the alternating spin locking sequence for 8 μs as shown in FIG. 8 on the left. A sweep of the source power through the Hartmann-Hahn double resonance while counting all the photons yielded the trace shown in FIG. 8 on the right. The low frequency components in the spin-locking signal for various microwave driving fields is shown on the x-axis, the corresponding Rabi frequency is shown on the y-axis. The oscillations appearing in the spectrum at the Hartmann-Hahn condition (when the Rabi frequency of electron spin matches the nuclear spin Larmor frequency) indicate flip-flops between electron spins and nuclear spins.

REFERENCE NUMBER LIST 1 diamond
2 magnet
3 colour centre
4 laser
5 magnet stage
6 microwave source
7 glass coverslip
8 optical path

The invention claimed is:

1. Method for hyperpolarisation of $^{13}$C nuclear spin in a diamond, comprising an optical pumping step, in which colour centre electron spins in the diamond are optically pumped, wherein in a transfer step, the polarisation of a long-lived state of the colour centre electron spins is transferred to $^{13}$C nuclear spins in the diamond via a long-range interaction.

2. The method according to claim 1, wherein the transfer step involves an application of a microwave field or a radio frequency (RF) field.

3. The method according to claim 2, wherein the microwave field or the RF field is pulsed.

4. The method according to claim 1, wherein the colour centre electron spin polarisation is transferred to the $^{13}$C nuclear spins in the diamond via a long-range interaction while fulfilling the Harman-Hahn condition.

5. The method according to claim 4, wherein the Hartmann-Hahn condition is achieved by a microwave field, the intensity of which field is chosen to match an energy difference between dressed colour centre electronic spin eigenstates and the $^{13}$C nuclear spins in an external magnetic field.

6. The method according to claim 5, wherein a magnetic flux density of the external magnetic field is smaller than 3 T.

7. The method according to claim 1, wherein the transfer step is performed by an excitation of selective transitions caused by a dipolar interaction of $^{13}$C nuclear spin states with the colour centre spin.

8. The method according to claim 1, wherein the transfer step is performed by interaction comprising at least two colour centre spins and a nuclear spin.

9. The method according to claim 1, wherein the colour centre is a nitrogen vacancy centre.

10. The method according to claim 1, wherein the optical pumping step and the transfer step are repeated cyclically.

11. The method according to claim 10, wherein after each cycle, a pause allows for the nuclear spin polarisations to spread throughout the diamond.

12. The method according to claim 1, wherein the method is carried out for less than 10 minutes.

13. The method according to claim 1, wherein the optical pumping step is performed with at least one laser pulse.

14. The method according to claim 1, wherein the diamond is a synthetic diamond.

15. The method according to claim 1, wherein the diamond has volume of between 50 $nm^3$ and 1 $cm^3$.

16. The method according to claim 1, wherein the diamond is coated with a non-diamond material.

17. A method for the nuclear spin hyperpolarisation of nuclear spins in a molecule, wherein the molecule is brought near or into contact with a diamond and prior to, during or after that, the diamond is hyperpolarised in a method according to claim 1.

18. Method for producing an imaging agent, wherein a diamond is coupled to a molecule and prior to, during or after the coupling, the diamond is hyperpolarised in the method according to claim 1.

19. Use of a hyperpolarised diamond according to claim 1 in medical or cell based imaging, in a quantum information processor or a quantum sensor based on spin degrees of freedom.

20. Diamond with a volume of above 1 $nm^3$, in which the $^{13}C$ nuclear spin polarisation is greater than 0.001%.

* * * * *